United States Patent
Morimoto et al.

(10) Patent No.: US 10,321,816 B2
(45) Date of Patent: Jun. 18, 2019

(54) LIGHT SOURCE DEVICE AND ENDOSCOPE SYSTEM

(71) Applicant: FUJIFILM Corporation, Tokyo (JP)

(72) Inventors: Yoshinori Morimoto, Kanagawa (JP); Satoshi Ozawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/599,475

(22) Filed: May 19, 2017

(65) Prior Publication Data
US 2017/0360287 A1    Dec. 21, 2017

(30) Foreign Application Priority Data

Jun. 17, 2016 (JP) ................................. 2016-121102
Apr. 25, 2017 (JP) ................................. 2017-086445

(51) Int. Cl.
*F21V 5/00* (2018.01)
*G02B 21/00* (2006.01)
(Continued)

(52) U.S. Cl.
CPC ........ *A61B 1/0684* (2013.01); *A61B 1/00006* (2013.01); *A61B 1/00009* (2013.01);
(Continued)

(58) Field of Classification Search
CPC ....... G06T 7/90; G06T 7/0012; G06T 11/001; G06K 9/0014; A61B 1/00009;
(Continued)

(56) References Cited

U.S. PATENT DOCUMENTS

2012/0147166 A1    6/2012  Minetoma et al.
2013/0012794 A1*   1/2013  Zeng ................... A61B 1/00186
                                                        600/328
(Continued)

FOREIGN PATENT DOCUMENTS

EP    2926718    10/2015
JP    2004-121486   4/2004
(Continued)

OTHER PUBLICATIONS

"Search Report of European Counterpart Application," dated Nov. 17, 2017, p. 1-p. 7.
(Continued)

*Primary Examiner* — Thien T Mai
(74) *Attorney, Agent, or Firm* — JCIPRNET

(57) ABSTRACT

There are provided a light source device, which is more compact and inexpensive than a known light source device, and an endoscope system having a compact and inexpensive light source device. In a light source device, a light source unit includes a first light source that emits blue light, a second light source that emits broadband green light including not only a green component but also a red component, and an optical filter that adjusts the amount of broadband green light for each wavelength. The optical filter has a characteristic in which the reflectance of the green component is smaller than the reflectance of the red component in the case of reflecting the broadband green light or a characteristic in which the transmittance of the green component is smaller than the transmittance of the red component in the case of transmitting the broadband green light.

20 Claims, 15 Drawing Sheets

(51) Int. Cl.
*A61B 1/06* (2006.01)
*H01L 27/32* (2006.01)
*H04L 5/00* (2006.01)
*A61B 1/00* (2006.01)
*A61B 1/045* (2006.01)
*A61B 1/05* (2006.01)
*A61B 1/07* (2006.01)
*G02B 23/24* (2006.01)
*G01N 21/45* (2006.01)
*G02B 23/26* (2006.01)

(52) U.S. Cl.
CPC .......... *A61B 1/00188* (2013.01); *A61B 1/045* (2013.01); *A61B 1/05* (2013.01); *A61B 1/0638* (2013.01); *A61B 1/0646* (2013.01); *A61B 1/0653* (2013.01); *A61B 1/0669* (2013.01); *A61B 1/07* (2013.01); *G02B 23/24* (2013.01); *H01L 27/322* (2013.01); *H04L 5/0001* (2013.01); *G01N 2021/451* (2013.01); *G02B 23/26* (2013.01)

(58) Field of Classification Search
CPC ... A61B 1/0646; A61B 1/0638; A61B 5/0084; A61B 5/02007; A61B 1/0653; A61B 1/043; A61B 1/0684; A61B 1/0669; A61B 1/05; A61B 1/045; A61B 1/00188; A61B 1/00006; A61B 1/07; H04L 5/0001; H01L 27/322; G02B 23/24; G02B 23/26; G01N 2021/451
See application file for complete search history.

(56) References Cited

U.S. PATENT DOCUMENTS

| | | | | |
|---|---|---|---|---|
| 2013/0289373 | A1* | 10/2013 | Yamamoto | A61B 1/0638 600/339 |
| 2014/0316283 | A1* | 10/2014 | Kaku | A61B 1/0653 600/479 |
| 2015/0099932 | A1* | 4/2015 | Morimoto | H05B 33/0854 600/180 |
| 2017/0265731 | A1* | 9/2017 | Yoshizaki | A61B 1/00 |

FOREIGN PATENT DOCUMENTS

| | | |
|---|---|---|
| JP | 2016-007355 | 1/2016 |
| JP | 2016067373 | 5/2016 |
| WO | 2015016013 | 2/2015 |
| WO | 2015029709 | 3/2015 |

OTHER PUBLICATIONS

"Office Action of Europe Counterpart Application", dated Feb. 6, 2019, pp. 1-6.

* cited by examiner

FIG. 11

| B | G | B | G | ... |
|---|---|---|---|---|
| G | R | G | R | ... |
| B | G | B | G | ... |
| G | R | B | R | ... |
| ⋮ | ⋮ | ⋮ | ⋮ | |

FIG. 12

| R | G | R | G | ... |
|---|---|---|---|---|
| B | R | B | R | ... |
| R | G | R | G | ... |
| B | R | B | R | ... |
| ⋮ | ⋮ | ⋮ | ⋮ | |

FIG. 13

| Y | C | Y | C | ... |
|---|---|---|---|---|
| G | M | G | M | ... |
| Y | C | Y | C | ... |
| G | M | G | M | ... |
| ⋮ | ⋮ | ⋮ | ⋮ | |

FIG. 14

| Y | C | Y | C | ... |
|---|---|---|---|---|
| R | M | R | M | ... |
| Y | C | Y | C | ... |
| R | M | R | M | ... |
| ⋮ | ⋮ | ⋮ | ⋮ | |

FIG. 15

| G | C | G | C | ... |
|---|---|---|---|---|
| R | M | R | M | ... |
| G | C | G | C | ... |
| R | M | R | M | ... |
| ⋮ | ⋮ | ⋮ | ⋮ | |

FIG. 16

| Y | R | Y | R | ... |
|---|---|---|---|---|
| G | M | G | M | ... |
| Y | R | Y | R | ... |
| G | M | G | M | ... |
| ⋮ | ⋮ | ⋮ | ⋮ | |

LIGHT SOURCE DEVICE AND ENDOSCOPE SYSTEM

CROSS-REFERENCE TO RELATED APPLICATIONS

The present application claims priority under 35 U.S.C. § 119 to Japanese Patent Applications No. 2016-121102, filed on Jun. 17, 2016 and No. 2017-086445, filed on Apr. 25, 2017. Each of the above application(s) is hereby expressly incorporated by reference, in its entirety, into the present application.

BACKGROUND OF THE INVENTION

1. Field of the Invention

The present invention relates to a light source device, which generates illumination light for illuminating an observation target using light emitted from a plurality of light sources, and an endoscope system.

2. Description of the Related Art

In the medical field, it is common to perform diagnosis using an endoscope system including a light source device, an endoscope, and a processor device. The light source device generates white light as illumination light, for example. The endoscope images an observation target irradiated with illumination light. The processor device generates an image for observation (hereinafter, referred to as an observation image), which is used for diagnosis, using an image (hereinafter, referred to as a captured image) of the observation target captured by the endoscope, and displays the observation image on a monitor.

In the light source device used in the endoscope system, white illumination light emitted from a lamp, such as a xenon lamp, is used as in JP2004-121486A, for example. In recent years, however, a light source device that emits white illumination light using a semiconductor light source, such as a light emitting diode (LED), is known (JP2016-007355A). As in JP2004-121486A and JP2016-007355A, in the light source device of the endoscope system, there is a case where a component of light included in illumination light is adjusted using an optical filter.

SUMMARY OF THE INVENTION

In the case of emitting illumination light using a semiconductor light source, such as an LED, it is required to be able to observe the observation target as in the case of using a known light source device that emits illumination light using a lamp. However, in order to reproduce an observation image, which is captured by illumination light emitted from a known lamp, using illumination light emitted from a single color light source such as an LED, it is necessary to use light sources of a plurality of colors. That is, it is necessary to arrange light sources of at least three primary colors. For example, in the case of using an LED as a light source of illumination light, it is necessary to mount blue, green, and red LEDs in the light source device. In addition, in order to further enhance the reproducibility of the observation image or to realize other special observation modes, it is necessary to add light sources of other colors in addition to these.

As described above, by providing light sources of various colors in the light source device, it is possible to reproduce an observation image in the case of using a lamp or to realize a special observation mode. However, there is a problem that, as the number of colors of light sources increases, the size of the light source device increases due to arrangement space for the light sources and the manufacturing cost also increases.

It is an object of the invention to provide a light source device, which is more compact and inexpensive than a known light source device, and an endoscope system having a compact and inexpensive light source device.

A light source device comprises: a first light source that emits blue light; a second light source that emits broadband green light including not only a green component but also a red component; and an optical filter that adjusts an amount of the broadband green light for each wavelength. The optical filter has a characteristic in which the reflectance of the green component is smaller than the reflectance of the red component in the case of reflecting the broadband green light or a characteristic in which the transmittance of the green component is smaller than the transmittance of the red component in the case of transmitting the broadband green light.

It is preferable that the second light source includes a light emitting element that emits excitation light and a fluorescent substance that emits the broadband green light when the excitation light is emitted thereto and that the optical filter cuts the excitation light.

It is preferable that the optical filter has a reflectance or a transmittance for each component that changes stepwise.

It is preferable that the optical filter has a reflectance or a transmittance for each component that changes smoothly.

It is preferable that the optical filter is a multiplexing member that combines the blue light and the broadband green light.

It is preferable to comprise, in addition to the first and second light sources, an additional light source that emits light having a difference in light absorption coefficient between oxygenated hemoglobin and reduced hemoglobin.

It is preferable to comprise, in addition to the first and second light sources, an additional light source that emits infrared light.

It is preferable to comprise, in addition to the optical filter or in an exchangeable manner with the optical filter, a second optical filter that attenuates the red component from the broadband green light.

An endoscope system comprises: a light source device which has a first light source that emits blue light, a second light source that emits broadband green light including not only a green component but also a red component, and an optical filter that adjusts an amount of the broadband green light for each wavelength and in which the optical filter has a characteristic, in which a reflectance of the green component is smaller than a reflectance of the red component in a case of reflecting the broadband green light, or a characteristic, in which a transmittance of the green component is smaller than a transmittance of the red component in a case of transmitting the broadband green light; and an image sensor that images an observation target using the blue light and the broadband green light whose components have been adjusted by the optical filter.

It is preferable that the image sensor is a color sensor having a color filter for each pixel.

It is preferable that a gain applied to a red image obtained by imaging the observation target using the red component is larger than a gain applied to a green image obtained by imaging the observation target using the green component.

The light source device of the invention has the first light source, which emits the blue light, and the second light source, which emits the broadband green light including not only the green component but also the red component, as light sources, and forms white illumination light as a whole by adjusting the amount of broadband green light for each wavelength using the optical filter. Therefore, the light source device and the endoscope system of the invention are more compact and inexpensive than those in the related art since a red light source that emits red light can be omitted.

BRIEF DESCRIPTION OF THE DRAWINGS

FIG. 11 is an arrangement of known primary color system color filters.
FIG. 12 is an arrangement of primary color system color filters to reduce the sensitivity of a green component G and increase the sensitivity of a red component R.
FIG. 13 is an arrangement of known complementary color system color filters.
FIG. 14 is an arrangement of complementary color system color filters to reduce the sensitivity of the green component G and increase the sensitivity of the red component R.
FIG. 15 is an arrangement of complementary color system color filters to increase the sensitivity of the red component R.
FIG. 16 is an arrangement of complementary color system color filters to increase the sensitivity of the red component R.

DESCRIPTION OF THE PREFERRED EMBODIMENTS

[First Embodiment]

Figure 1:
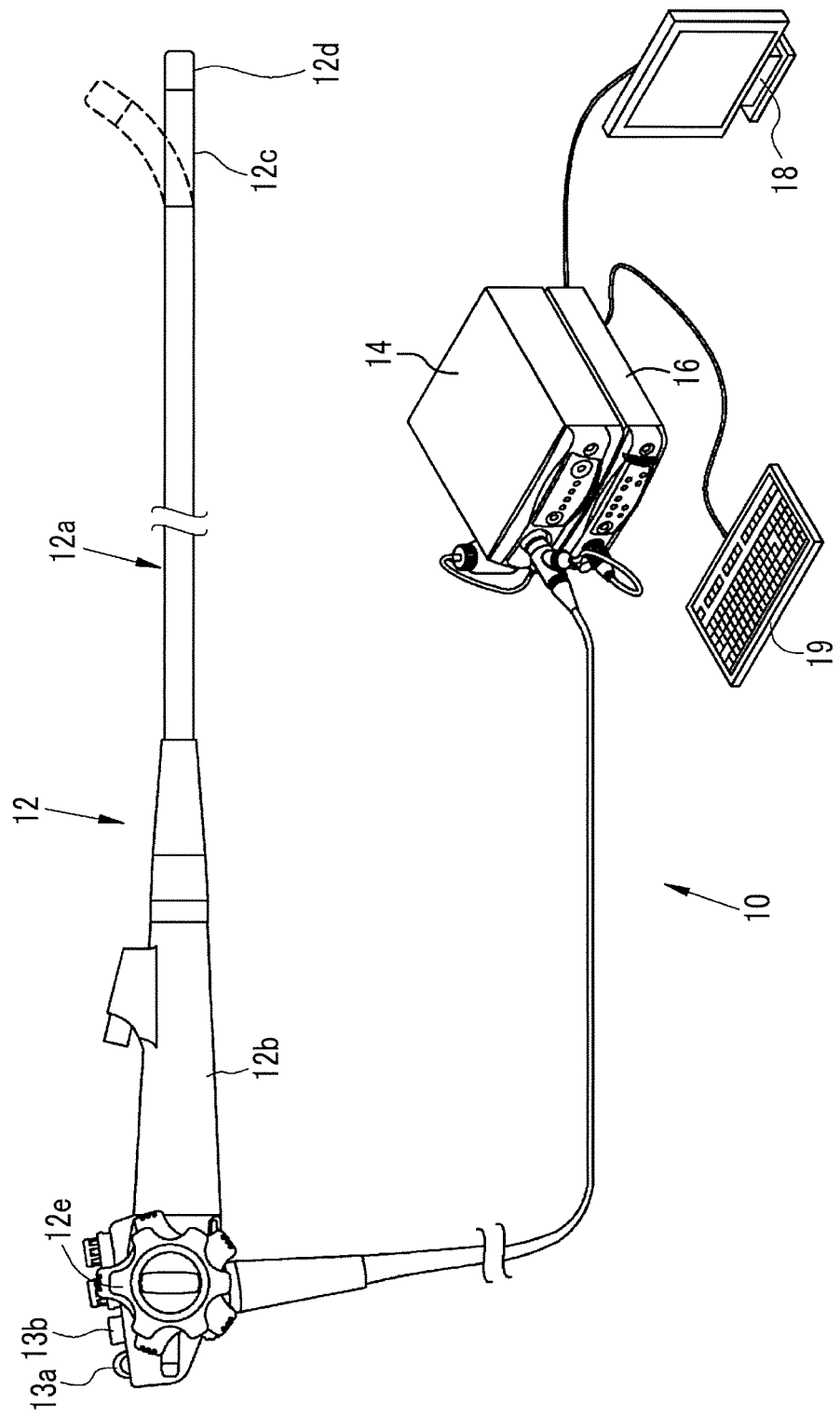
FIG. 1 is a schematic diagram of an endoscope system.

As shown in FIG. 1, an endoscope system 10 has an endoscope 12 for imaging an observation target, a light source device 14, a processor device 16, a monitor 18 that is a display unit, and a console 19. The endoscope 12 is optically connected to the light source device 14, and is electrically connected to the processor device 16. The endoscope 12 has an insertion portion 12a that is inserted into a subject, an operation portion 12b provided in a proximal end portion of the insertion portion 12a, and a bending portion 12c and a distal end portion 12d that are provided at the distal end side of the insertion portion 12a. By operating an angle knob 12e of the operation portion 12b, the bending portion 12c is bent. As a result of the bending of the bending portion 12c, the distal end portion 12d faces in a desired direction. An injection port (not shown) for injecting air, water, or the like toward the observation target is provided in the distal end portion 12d. In addition to the angle knob 12e, a zoom operation portion 13a and a mode selector switch 13b are provided in the operation portion 12b. The zoom operation portion 13a is used when enlarging or reducing the observation target. The mode selector switch 13b is used to switch the observation mode in a case where the endoscope system 10 has a plurality of observation modes.

The processor device 16 is electrically connected to the monitor 18 and the console 19. The monitor 18 outputs and displays an observation image, additional image information, and the like when necessary. The console 19 functions as a user interface for receiving an input operation, such as a function setting. In addition, an external recording unit (not shown) in which an image, image information, and the like are recorded may be connected to the processor device 16.

Figure 2:
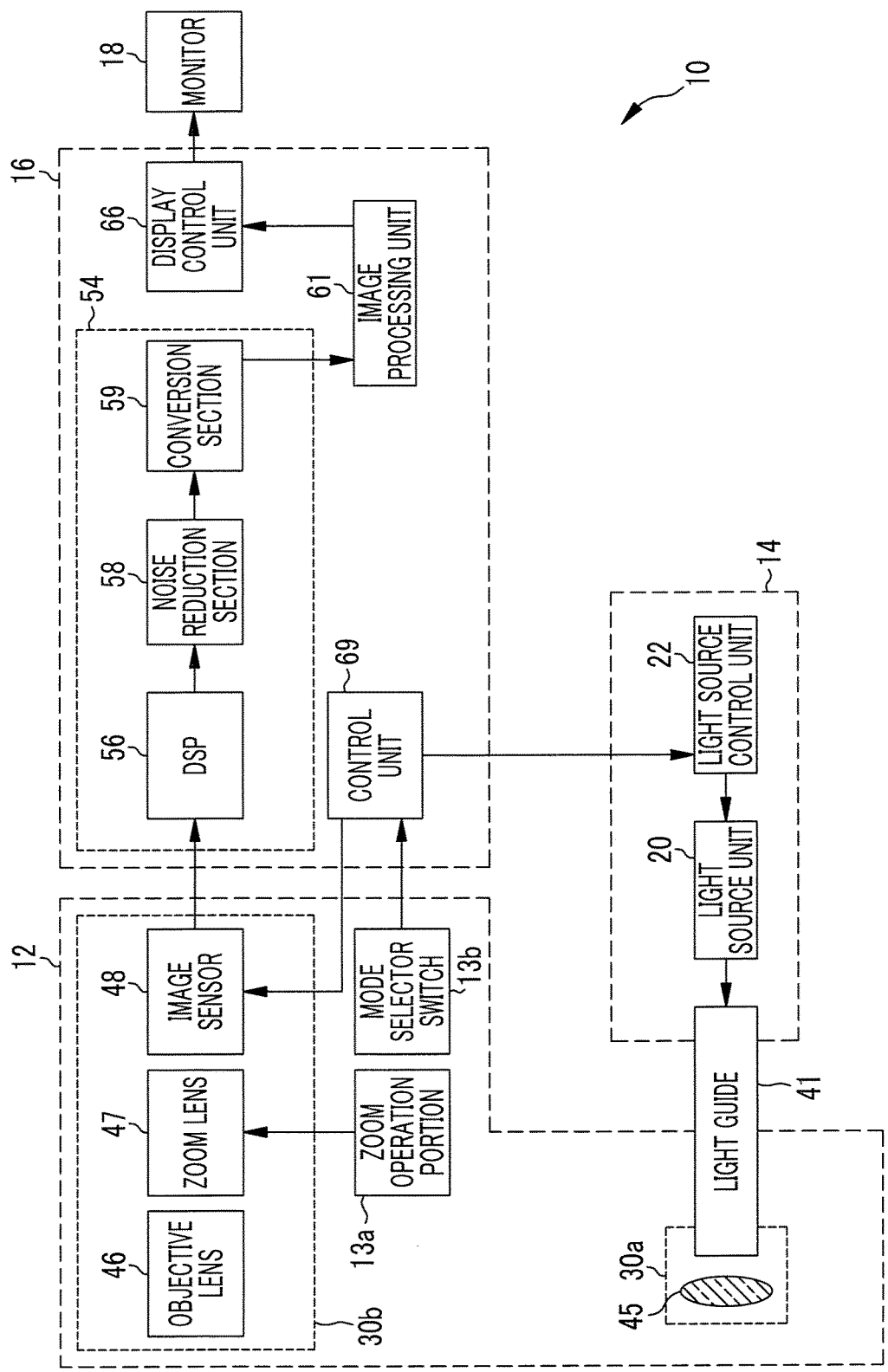
FIG. 2 is a block diagram of the endoscope system.

As shown in FIG. 2, the light source device 14 includes a light source unit 20 that emits illumination light and a light source control unit 22 that controls the emission timing of illumination light, the amount of illumination light, components of illumination light, and the like. In the present embodiment, the illumination light is usually white light.

The illumination light emitted from the light source unit 20 is incident on a light guide 41. The light guide 41 is built into the endoscope 12 and a universal cord, and propagates the illumination light to the distal end portion 12d of the endoscope 12. The universal cord is a cord for connecting the endoscope 12 with the light source device 14 and the processor device 16. As the light guide 41, it is possible to use a multi-mode fiber. As an example, it is possible to use a small-diameter fiber cable having a diameter of ϕ0.3 mm to ϕ0.5 mm that includes a core with a diameter of 105μm, a cladding with a diameter of 125μm, and a protective layer as an outer skin.

An illumination optical system 30a and an imaging optical system 30b are provided in the distal end portion 12d of the endoscope 12. The illumination optical system 30a has an illumination lens 45, and illumination light is emitted to the observation target through the illumination lens 45. The imaging optical system 30b has an objective lens 46, a zoom lens 47, and an image sensor 48. The image sensor 48 images the observation target using reflected light (including scattered light, fluorescence emitted from the observation target, fluorescence due to medicine administered to the observation target, or the like in addition to the reflected light) of the illumination light that returns from the observation target through the objective lens 46 and the zoom lens 47. The zoom lens 47 is moved by operating the zoom operation portion 13*a*. As a result, the observation target to be imaged using the image sensor 48 is enlarged or reduced for observation.

Figure 3:
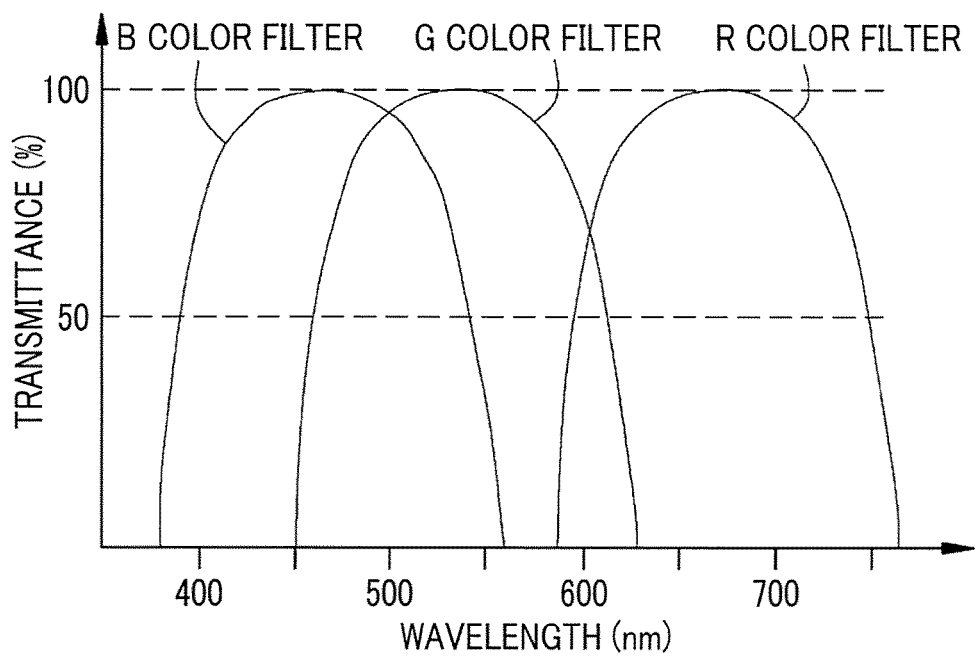
FIG. 3 is a graph showing the transmittance of a color filter.

In the present embodiment, the image sensor 48 is a so-called primary color system color sensor having a color filter in each pixel. For this reason, each pixel of the image sensor 48 has any one of an R color filter (red color filter), a G color filter (green color filter), and a B color filters (blue color filter) shown in FIG. 3, for example. A pixel having an R color filter is an R pixel, a pixel having a G color filter is a G pixel, and a pixel having a B color filter is a B pixel. Thus, the image sensor 48 has pixels of three colors of R pixel, G pixel, and B pixel. Accordingly, in the case of imaging the observation target using white light as illumination light, an R image obtained by imaging the observation target with the R pixel, a G image obtained by imaging the observation target with the G pixel, and a B image obtained by imaging the observation target with the B pixel are obtained at the same time.

As the image sensor 48, it is possible to use a charge coupled device (CCD) sensor or a complementary metal oxide semiconductor (CMOS) sensor. Although the image sensor 48 of the present embodiment is a primary color system color sensor, it is also possible to use a complementary color system color sensor. For example, the complementary color system color sensor includes a cyan pixel in which a cyan color filter is provided, a magenta pixel in which a magenta color filter is provided, a yellow pixel in which a yellow color filter is provided, and a green pixel in which a green color filter is provided. Images obtained from the pixels of the respective colors described above in the case of using the complementary color system color sensor can be converted into a B image, a G image, and an R image by performing complementary color-primary color conversion. Instead of the color sensor, a monochrome sensor in which no color filter is provided can be used as the image sensor 48. In this case, by sequentially imaging the observation target using the illumination light of respective colors, such as BGR, it is possible to obtain images of the respective colors described above.

The processor device 16 has an image acquisition unit 54, an image processing unit 61, a display control unit 66, and a control unit 69.

The image acquisition unit 54 acquires captured images of a plurality of colors obtained by imaging the observation target using the image sensor 48. Specifically, the image acquisition unit 54 acquires a set of B image, G image, and R image for each imaging frame. The image acquisition unit 54 has a digital signal processor (DSP) 56, a noise reduction section 58, and a conversion section 59, and performs various kinds of processing on the acquired images using these.

The DSP 56 performs various kinds of processing, such as defect correction processing, offset processing, gain correction processing, linear matrix processing, gamma conversion processing, demosaic processing, and YC conversion processing, on the acquired images when necessary.

The defect correction processing is processing for correcting the pixel value of each pixel corresponding to the defective pixel of the image sensor 48. The offset processing is processing for setting an accurate zero level by reducing a dark current component from the image subjected to the defect correction processing. The gain correction processing is processing for adjusting the signal level of each image by multiplying the image subjected to the offset processing by the gain. The linear matrix processing is processing for improving the color reproducibility of the image subjected to the offset processing, and the gamma conversion processing is processing for adjusting the brightness or the saturation of the image after the linear matrix processing. The demosaic processing (also referred to as isotropic processing or simultaneous processing) is processing for interpolating the pixel values of missing pixels, and is applied to the image after the gamma conversion processing. The missing pixel is a pixel having no pixel value because pixels of other colors are arranged in the image sensor 48 for the arrangement of color filters. For example, since the B image is obtained by imaging the observation target in the B pixel, a pixel at a position corresponding to the G or R pixel of the image sensor 48 has no pixel value. The demosaic processing is for generating the pixel values of pixels at the positions of the G and R pixels of the image sensor 48 by interpolating the B image. The YC conversion processing is processing for converting the image after the demosaic processing into a brightness channel Y, a color difference channel Cb, and a color difference channel Cr.

The noise reduction section 58 performs noise reduction processing on the brightness channel Y, the color difference channel Cb, and the color difference channel Cr using, for example, a moving average method or a median filter method. The conversion section 59 reconverts the brightness channel Y, the color difference channel Cb, and the color difference channel Cr after the noise reduction processing into images of the respective colors of BGR.

The image processing unit 61 generates an observation image by performing color conversion processing, color emphasis processing, and structure emphasis processing on the B image, the G image, and the R image for one imaging frame subjected to the various kinds of processing described above. In the color conversion processing, 3×3 matrix processing, gradation conversion processing, three-dimensional look-up table (LUT) processing, and the like are performed on the images of the respective colors of BGR. The color emphasis processing is processing for emphasizing the color of the image, and the structure emphasis processing is processing for emphasizing the tissue or structure of the observation target, such as a blood vessel or a pit pattern, for example.

The display control unit 66 acquires observation images from the image processing unit 61 in a sequential manner, converts the acquired observation images into a format suitable for display, and sequentially outputs and displays the converted observation images on the monitor 18. As a result, a doctor or the like can observe the observation target using a still image or a motion picture of the observation image.

The control unit 69 is, for example, a central processing unit (CPU), and performs overall control of the endoscope system 10, such as synchronous control of the illumination light emission timing and the imaging frame. In a case where the endoscope system 10 has a plurality of observation modes, the control unit 69 switches the illumination light through the light source control unit 22 by receiving an operation input from the mode selector switch 13*b*. *As a result, the observation mode is switched.*

Figure 4:
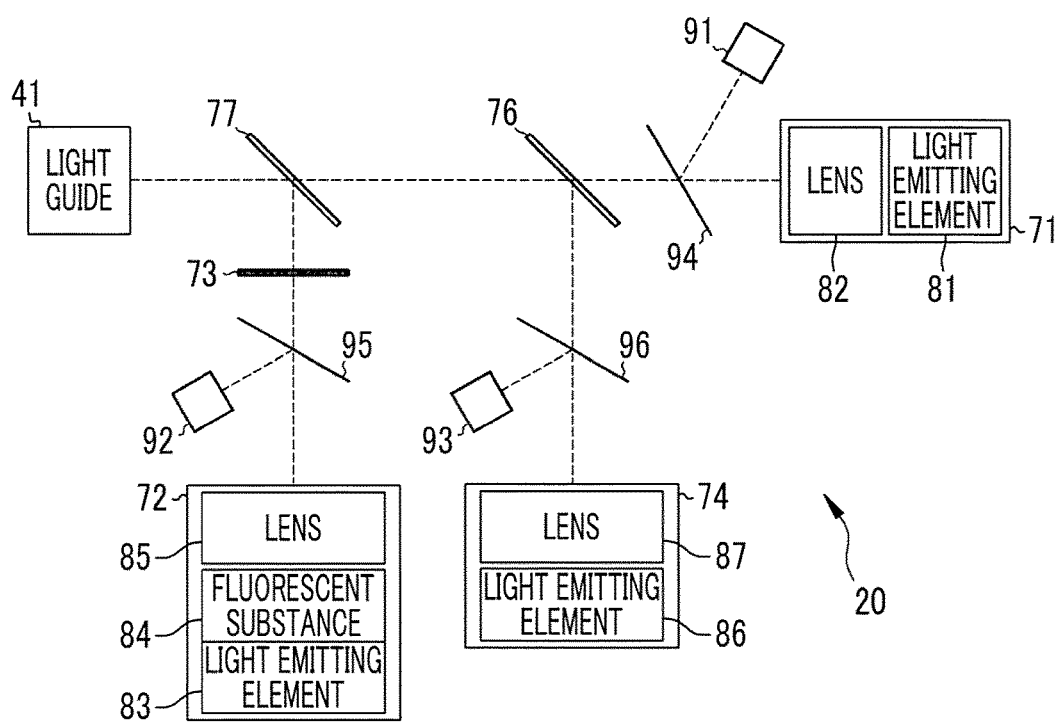
FIG. 4 is a block diagram of a light source unit provided in a light source device.

Hereinafter, the configuration and operation of the light source device 14 will be described in more detail. As shown in FIG. 4, the light source unit 20 of the light source device 14 includes a first light source 71, a second light source 72, and an optical filter 73. In the present embodiment, the light source unit 20 includes an additional light source 74 in addition to the first light source 71 and the second light source 72. The first light source 71, the second light source 72, and the additional light source 74 can be independently controlled.

The first light source 71 emits light of a blue component B (hereinafter, referred to as blue light). The first light source 71 includes a light emitting element 81 and a lens 82 for arranging blue light emitted from the light emitting element 81 into parallel light or the like. The light emitting element 81 is, for example, a semiconductor element, such as an LED or a laser diode (LD). The blue light emitted from the first light source 71 is incident on the light guide 41 through multiplexing members 76 and 77 that transmit blue light. The multiplexing members 76 and 77 are, for example, dichroic mirrors or dichroic prisms.

In general, the wavelength of blue is about 445 nm to about 485 nm. For example, there is a case where a color intermediate between blue and green is referred to as blue green so as to be distinguished from blue. In the endoscope system 10, however, it is not necessary to excessively subdivide the type of color (name of color) at least for light emitted from each light source of the light source unit 20. Therefore, in this specification, the color of light having a wavelength of about 440 nm or more and about 490 nm or less is referred to as blue color. In addition, the color of light having a wavelength greater than about 490 nm and less than about 600 nm is referred to as green, and the color of light having a wavelength equal to or greater than about 600 nm and less than about 680 nm is referred to as red. The color of visible light having a wavelength less than "about 440 nm" that is the lower limit of the blue wavelength (for example, visible light having a wavelength equal to or greater than about 380 nm and less than about 440 nm) is referred to as violet, and the color of light which has a shorter wavelength than violet and for which the image sensor 48 has sensitivity is refereed to as ultraviolet. The color of light which has a wavelength of "about 680 nm", which is the upper limit of the red wavelength, or more and for which the image sensor 48 has sensitivity is referred to as infrared. In this specification, "broadband" means that the wavelength range extends over a plurality of color wavelength ranges. White refers to the color of light including at least light belonging to the blue or violet color, light belonging to the green color, and light belonging to the red color.

The second light source 72 emits broadband light including a red component R in addition to a green component G. However, since light emitted from the second light source 72 has a greater amount of green component G than the amount of red component R, the light emitted from the second light source 72 is usually green if viewed. In this specification, therefore, the light emitted from the second light source 72 is referred to as green light. That is, the second light source 72 is a light source that emits broadband green light.

Figure 5:
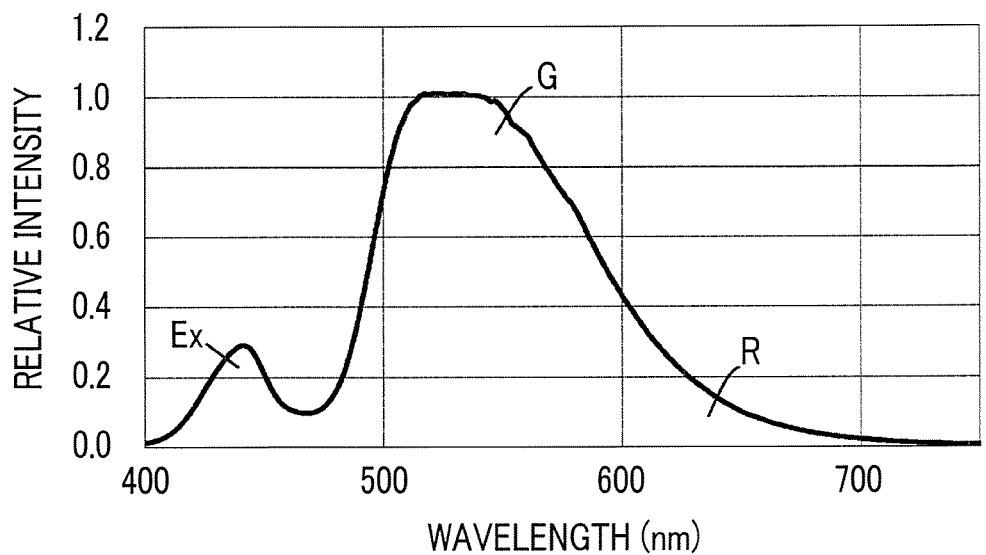
FIG. 5 is a graph showing the spectral spectrum of broadband green light emitted from a second light source.

The second light source 72 includes a light emitting element 83 that emits excitation light Ex, a fluorescent substance 84 that emits green light when the excitation light Ex emitted from the light emitting element 83 is incident thereon, and a lens 85 for arranging the broadband green light emitted from the fluorescent substance 84 into parallel light or the like. The light emitting element 83 is, for example, a semiconductor element, such as an LED or an LD. As shown in FIG. 5, the excitation light Ex is blue light having a peak at about 445 nm, and the green light emitted from the fluorescent substance 84 is broadband green light including the red component R in addition to the green component G. The broadband green light emitted from the second light source 72 as described above is incident on the light guide 41 through the optical filter 73 and the multiplexing member 77 that reflects the green component G and the red component R.

Figure 6:
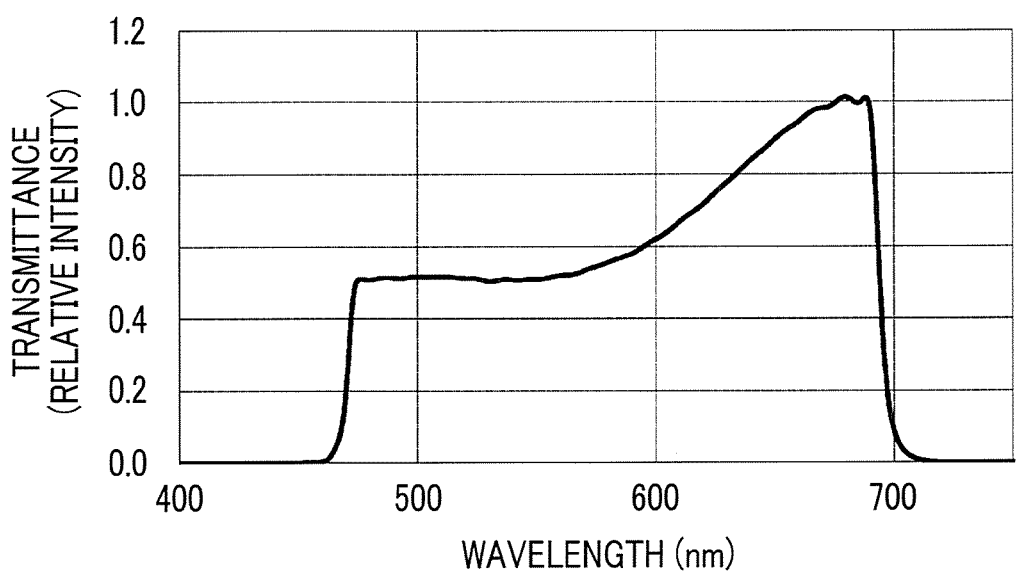
FIG. 6 is a graph showing the characteristics of an optical filter.
Figure 7:
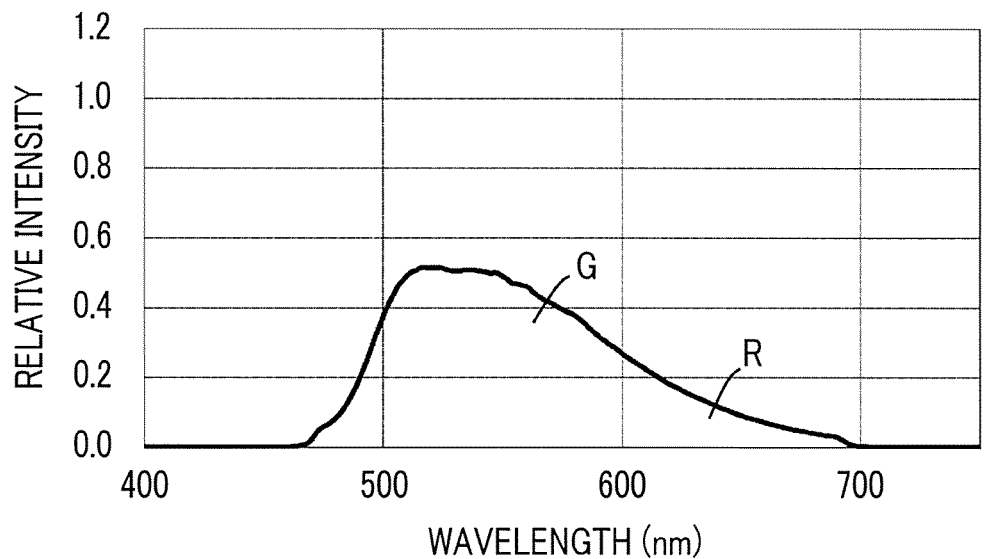
FIG. 7 is a graph showing the spectral spectrum of broadband green light transmitted through the optical filter.

The optical filter 73 has a spectral transmittance shown in FIG. 6. Therefore, as shown in FIG. 7, the optical filter 73 adjusts the amount of broadband green light, which is emitted from the second light source 72, for each wavelength. More specifically, the optical filter 73 adjusts the light amount ratio R/G between the green component G and the red component R of the broadband green light emitted from the second light source 72.

For example, in the present embodiment, the light amount ratio R/G between the green component G and the red component R of the broadband green light emitted from the second light source 72 is about 0.15. On the other hand, due to the optical filter 73, the light amount ratio R/G between the green component G and the red component R of the broadband green light becomes about 0.22 when the broadband green light is incident on the light guide 41. In a case where the light amount of the green component G of the broadband green light emitted from the second light source 72 (that is, before passing through the optical filter 73) is set to "Gb" and the amount of green light after passing through the optical filter 73 is set to "Ga", the light amount ratio Ga/Gb between the green component G before passing through the optical filter 73 and the green component G after passing through the optical filter 73 is about 0.52. In a case where the light amount of the red component R of the broadband green light emitted from the second light source 72 is set to "Rb" and the amount of red light after passing through the optical filter 73 is set to "Ra", the light amount ratio Ra/Rb between the red component R before passing through the optical filter 73 and the red component R after passing through the optical filter 73 is about 0.75.

As described above, the reason why the optical filter 73 adjusts the light amount ratio R/G between the green component G and the red component R of the broadband green light is to convert the illumination light into white light suitable for imaging the observation target. The white light suitable for imaging the observation target is, for example, white light used as illumination light in a known endoscope system. The light source device 14 of the endoscope system 10 includes the first light source 71 that emits blue light and the second light source 72 that emits broadband green light, but does not have a light source that emits red light. Therefore, although the red component R is included in the broadband green light, if the blue light and the broadband green light are simply combined to form illumination light, the red component R is insufficient relative to the blue component B and the green component G in the illumination light after the combination. For this reason, the illumination light after the combination becomes, for example, cyan (light blue). As a result, the color of the observation image becomes unnatural.

On the other hand, by adjusting the light amount ratio R/G between the green component G and the red component R of the broadband green light as described above using the optical filter 73, the light amount ratio between at least the green component G and the red component R included in the illumination light becomes a light amount ratio suitable for imaging the observation target. The amount of blue light of the first light source 71 and the amount of broadband green light of the second light source 72 can be independently controlled. Therefore, by adjusting the light amount ratio R/G between the green component G and the red component R of the broadband green light as described above using the optical filter 73 and appropriately adjusting the light emission amount of the first and second light sources 71 and 72 using the light source control unit 22, the illumination light becomes white light suitable for imaging the observation target.

A specific adjustment target value of the light amount ratio R/G is determined in consideration of the spectral characteristics of the broadband green light emitted from the second light source 72, the spectral characteristics of the color filter of each color of the image sensor 48, a gain when acquiring an image from the image sensor 48, the content of various kinds of processing (for example, a matrix used in linear matrix processing) performed by the DSP 56, and the like. As a result, the optical filter 73 adjusts a brightness ratio between the G image and the R image. Therefore, when the light amount ratio between the green component G and the red component R of the broadband green light is adjusted using the optical filter 73, a brightness ratio between the G image and the R image obtained in the case of imaging the observation target using white light as an adjustment target becomes almost equal to a brightness ratio between the G image and the R image obtained in the case of imaging the observation target using the illumination light generated by the light source device 14. That is, the light source device 14 does not have a red light source that emits red light, but the obtained observation image has the same color tone as an observation image obtained in the case of imaging the observation target using the white light as an adjustment target.

Since the illumination light is converted into white light using the red component R, which is a part on the long wavelength side of the broadband green light of the second light source 72, instead of providing a red light source for emitting red light in the light source unit 20 as described above, the amount of green component G becomes much larger than the amount of red component R. Therefore, for the spectral transmittance (refer to FIG. 6) of the optical filter 73, at least the transmittance of the green component G is lower than the transmittance of the red component R. In the present embodiment, the optical filter 73 transmits the broadband green light emitted from the second light source 72 and guides the broadband green light to the light guide 41. However, it is needless to say that the optical filter 73 can reflect the broadband green light and guide the broadband green light to the light guide 41. In this case, the spectral reflectance of the optical filter 73 is the same as, for example, that in FIG. 6, and at least the reflectance of the green component is lower than the reflectance of the red component. That is, the optical filter 73 has a characteristic (spectral reflectance) in which at least the reflectance of the green component G is lower than the reflectance of the red component R in the case of reflecting the broadband green light and guiding the broadband green light to the light guide 41, or has a characteristic (spectral reflectance) in which at least the transmittance of the green component G is lower than the transmittance of the red component R in the case of transmitting the broadband green light and guiding the broadband green light to the light guide 41.

Figure 8:
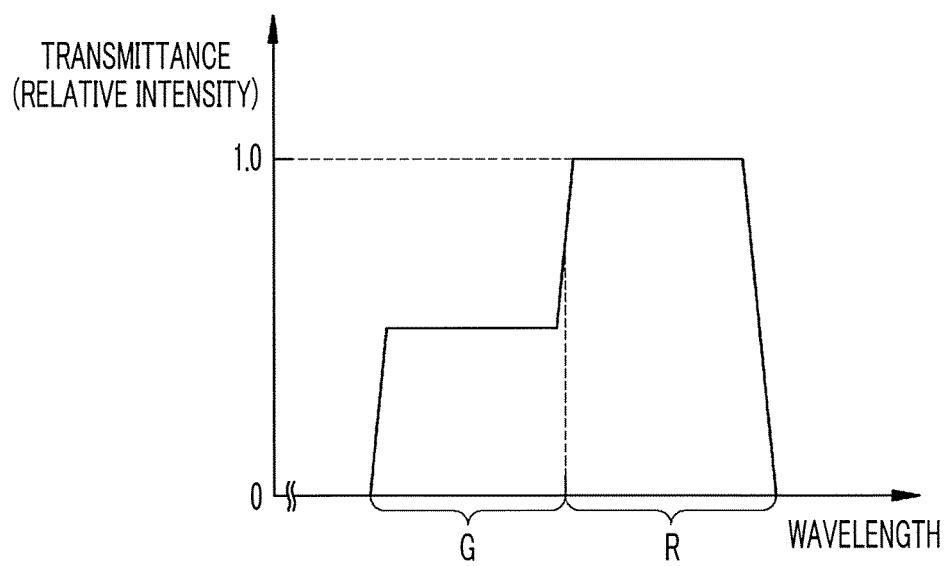
FIG. 8 is a graph showing the characteristics of an optical filter of a modification example.

The optical filter 73 has a transmittance for each wavelength that changes smoothly. Specifically, in the range of the green component G, the transmittance for each wavelength is substantially constant. In the range of the red component R, the transmittance for each wavelength gradually rises smoothly toward the long wavelength side. The spectral transmittance is determined in consideration of the reproducibility (ease of viewing) of a structure, such as a blood vessel. For example, in the endoscope system 10 and a known endoscope system, the depth or thickness of a blood vessel that is easily viewed changes according to the wavelength of light included in the illumination light. For this reason, if the spectral spectrum (light amount for each wavelength) of the illumination light is different, a blood vessel at certain depth and thickness may differ in ease of viewing. Therefore, the optical filter 73 smoothly changes the reflectance for each wavelength, and approximately reproduces almost the same spectral spectrum as the white light as an adjustment target in the range of the green component G and the red component R. In the case of configuring the optical filter 73 more easily, it is possible to make the change in transmittance for each wavelength stepwise. For example, as shown in FIG. 8, it is possible to adopt a configuration in which the spectral transmittance of the optical filter 73 is substantially constant in the wavelength range of the green component G and the wavelength range of the red component R. The spectral reflectance of the optical filter 73 in the case of reflecting broadband green light and guiding the broadband green light to the light guide 41 is also the same.

As can be seen from the spectral transmittance (see FIG. 6), the optical filter 73 also functions as an excitation light cut filter that cuts the excitation light Ex. Accordingly, a part of the excitation light Ex passes through the fluorescent substance 84 and is then incident on the optical filter 73, but is not incident on the light guide 41 since it is cut by the optical filter 73. Although the optical filter 73 and the multiplexing member 77 are separately provided in the present embodiment, the optical filter 73 and the multiplexing member 77 can be integrated. In this case, the optical filter 73 adjusts the light amount ratio between the green component G and the red component R when the broadband green light is reflected to be guided to the light guide 41, and also functions as a multiplexing member that combines the blue light or the like emitted from the first light source 71 with the broadband green light emitted from the second light source 72.

The additional light source 74 emits light including a violet component V (hereinafter, referred to as violet light). The additional light source 74 includes a light emitting element 86 and a lens 87 for arranging violet light emitted from the light emitting element 86 into parallel light or the like. The light emitting element 86 is, for example, a semiconductor element, such as an LED or an LD. The violet light emitted from the additional light source 74 is incident on the light guide 41 through the multiplexing member 76 that reflects violet light and the multiplexing member 77 that transmits violet light. The violet component V of violet light is received by the B pixel in the image sensor 48. For this reason, the reflected light of violet light and the like contribute to the B image together with the reflected light of blue light and the like.

In addition to the first light source 71, the second light source 72, the optical filter 73, and the additional light source 74, the light source unit 20 includes photodetectors 91, 92, and 93, beam splitters 94, 95, and 96, and a cooling member (so-called heat sink; not shown) for cooling the light emitting element of each light source. The beam splitter 94 reflects a part of blue light emitted from the first light source 71 at a predetermined ratio, and the photodetector 91 receives the blue light reflected by the beam splitter 94. The beam splitter 95 reflects a part of broadband green light emitted from the second light source 72 at a predetermined ratio, and the photodetector 92 receives the broadband green light reflected by the beam splitter 94. The beam splitter 96 reflects a part of violet light emitted from the additional light source 74 at a predetermined ratio, and the photodetector 93 receives the violet light reflected by the beam splitter 96. The light source control unit 22 controls the light emission amount of the blue light of the first light source 71 automatically and accurately using the light amount detected by the photodetector 91. In addition, the light source control unit 22 controls the light emission amount of the broadband green light of the second light source 72 automatically and accurately using the light amount detected by the photodetector 92. Similarly, the light source control unit 22 controls the light emission amount of the violet light of the additional light source 74 automatically and accurately using the light amount detected by the photodetector 93.

Figure 9:
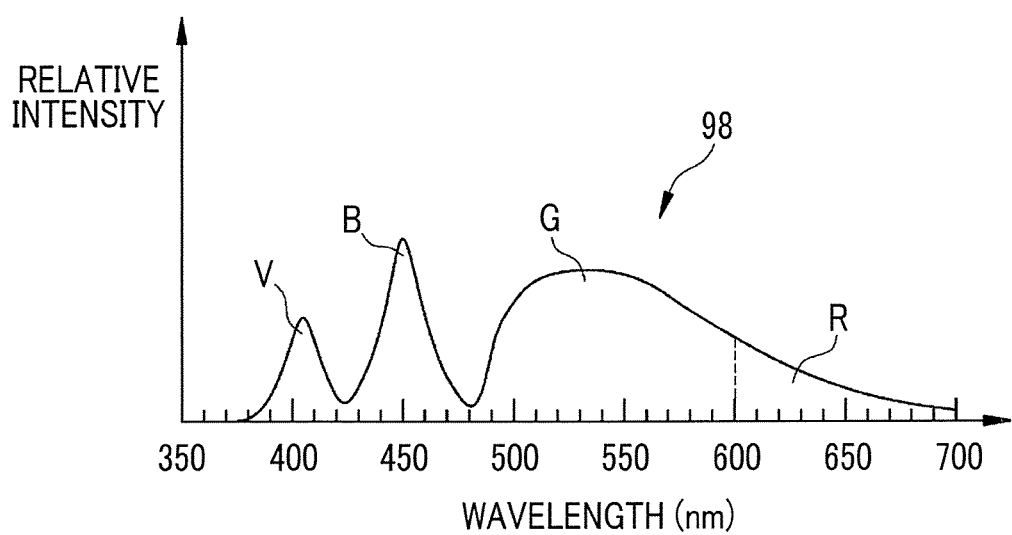
FIG. 9 is a spectral spectrum of illumination light.

The light source device 14 configured as described above emits almost white illumination light 98 shown in FIG. 9, for example. Then, the image sensor 48 images an observation target using the illumination light 98 including the blue light emitted from the light source device 14 and the broadband green light whose components have been adjusted by the optical filter 73.

The blue component B included in the illumination light 98 is the blue component B of the blue light emitted from the first light source 71, and the violet component V included in the illumination light 98 is the violet component V of the violet light emitted from the additional light source 74. For the green component G and the red component R included in the illumination light 98, the optical filter 73 adjusts the green component G and the red component R of the broadband green light emitted from the second light source 72 to a balance suitable for forming white light. That is, although the light source unit 20 does not have a red light source that emits red light, it is possible to form white illumination light using the red component R of the broadband green light as the red component R of the illumination light 98.

As described above, the light source device 14 can adjust the balance of the green component G and the red component R of the broadband green light using the optical filter 73, and can form the white illumination light 98 without providing a red light source for emitting red light in the light source unit 20 by using the red component R of the broadband green light. Therefore, the light source device 14 is more compact than a known light source device having a red light source to form white illumination light since it is not necessary to provide a red light source for emitting red light. In addition, the light source device 14 is less expensive than a known light source device having a red light source to form the white illumination light 98 since it is not necessary to provide a red light source for emitting red light.

Figure 10:
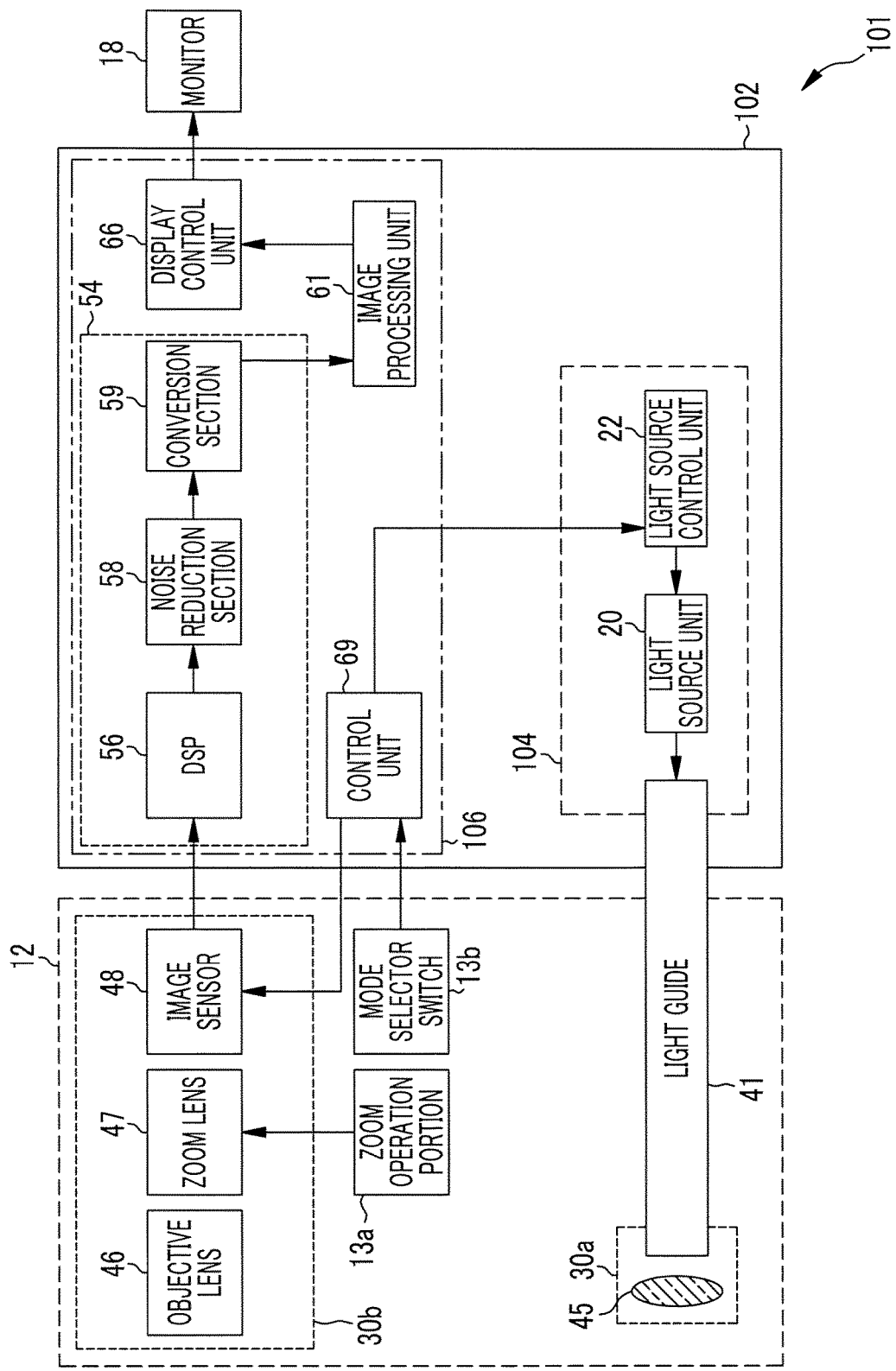
FIG. 10 is a block diagram of an endoscope system in which a light source device and a processor device are integrated.

In the embodiment described above, the light source device 14 and the processor device 16 are separate devices. However, since the light source device 14 of the invention is more compact than a known light source device, the light source device 14 and the processor device 16 can be integrated. For example, as shown in FIG. 10, an endoscope system 101 can be formed using an endoscope 12 and an integrated control device 102 which has a light source block 104 configured to include respective units of the light source device 14 and a processor block 106 configured to include respective units of the processor device 16 and in which the light source device 14 and the processor device 16 are integrated.

Although the additional light source 74 is provided in the embodiment described above, the additional light source 74 can be omitted. For example, in a case where violet light is not used for the imaging of the observation target, the size of the light source device 14 can be further reduced by omitting the additional light source 74.

In the embodiment described above, the optical filter 73 adjusts the light amount ratio RIG between the green component G and the red component R of the broadband green light, and as a result, adjusts the brightness ratio between the G image and the R image. However, it is possible to adjust the brightness ratio between the G image and the R image by combining the optical filter 73 and the arrangement of color filters of the image sensor 48. For example, as shown in FIG. 11, the color filters of the image sensor 48 are usually arranged in a ratio of R:G:B=1:2:1 in consideration of visibility. On the other hand, as shown in FIG. 12, if the number of G pixels is reduced and the number of R pixels is increased, for example, by setting R:G:B=2:1:1 for the color filters of the image sensor 48, it is possible to reduce the sensitivity of the green component G and increase the sensitivity of the red component R. Therefore, by using the image sensor 48 having a color filter arrangement shown in FIG. 12, it is possible to adjust the brightness ratio between the G image and the R image by combining the optical filter 73 and the arrangement of color filters of the image sensor 48. Although FIGS. 11 and 12 show the image sensor 48 having a square arrangement as an example, the same applies to a case of using the image sensor 48 having other arrangements, such as the image sensor 48 having a so-called honeycomb arrangement.

This is also the same as in a case of using the image sensor 48 having complementary color system color filters. As shown in FIG. 13, the image sensor 48 having complementary color system color filters has color filters of cyan (C), magenta (M), yellow (Y), and green (G) in a ratio of C:M:Y:G=1:1:1:1. Therefore, as shown in FIG. 14, for example, by replacing a green (G) color filter with a red (R) color filter, it is possible to reduce the sensitivity of the green component G and increase the sensitivity of the red component R. Then, by using the complementary color system image sensor 48 in which a green (G) color filter is replaced with a red (R) color filter, it is possible to adjust the brightness ratio between the G image and the R image by combining the optical filter 73 and the arrangement of color filters of the image sensor 48. In addition, although FIGS. 13 and 14 show the image sensor 48 having a square arrangement as an example, the same applies to a case of using the image sensor 48 having other arrangements, such as the image sensor 48 having a so-called honeycomb arrangement. In the case of the complementary color system image sensor 48, instead of replacing the green (G) color filter with the red (R) color filter as described above, a yellow (Y) color filter may be replaced with a red (R) color filter as shown in FIG. 15. As shown in FIG. 16, a cyan (C) color filter may be replaced with a red (R) color filter. In the arrangement shown in FIGS. 15 and 16, the sensitivity of the red component R can be increased relative to the sensitivity of the green component G. As a result, it is possible to adjust the brightness ratio between the G image and the R image by combining the optical filter 73 and the arrangement of color filters of the image sensor 48.

As described above, by adjusting the brightness ratio between the G image and the R image by combining the optical filter 73 and the arrangement of color filters of the image sensor 48, it is possible to prevent a situation in which the optical filter 73 reduces the green component G of the broadband green light too much in order to form white light, and as a result, the noise of the G image is increased.

In the embodiment described above, the optical filter 73 adjusts the light amount ratio R/G between the green component G and the red component R of the broadband green light, and as a result, adjusts the brightness ratio between the G image and the R image. However, it is possible to adjust the brightness ratio between the G image and the R image by combining the various kinds of processing of the optical filter 73 and the image acquisition unit 54 or the observation image generation processing of the image processing unit 61. Specifically, in a case where the light source device 14 is used, in the image acquisition unit 54 or the image processing unit 61, it is preferable to electronically increase the brightness of the R image by setting a gain applied to the R image, which is obtained by imaging the observation target using the red component R, to be larger than a gain applied to the G image, which is obtained by imaging the observation target using the green component G. Thus, in the case of electronically increasing the brightness of the R image, it is preferable to apply a low pass filter to the R image. This is because the R image originally has few images of blood vessels or the like and accordingly the influence on the observation image is small even if the brightness of the R image is electronically increased and the low pass filter is applied. Thus, by adjusting the brightness ratio between the G image and the R image by combining the optical filter 73, processing for increasing the brightness of the R image, and low pass filter processing, it is possible to prevent a situation in which the optical filter 73 reduces the green component G of the broadband green light too much in order to form white light, and as a result, the noise of the G image is increased.

Figure 17:
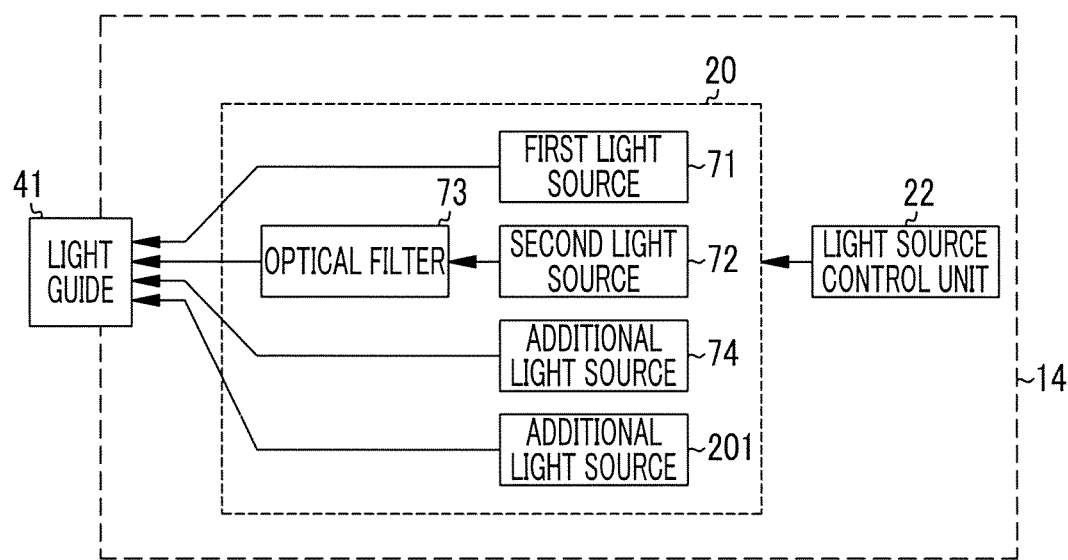
FIG. 17 is a block diagram of a light source device that further includes an additional light source.

Although the additional light source 74 for emitting violet light is provided in the embodiment as described above, an additional light source 201 can be further provided in the light source device 14 as shown in FIG. 17. The additional light source 201 has the same configuration as the additional light source 74 except that the additional light source 201 emits light other than the violet light in the above embodiment. The light source device 14 is compact since it is not necessary to provide a red light source for emitting red light. Accordingly, even if the additional light source 201 is further provided, it is possible to configure the light source device 14 with the same size as a known light source device. Needless to say, the light source device 14 can be formed more compactly than the known light source device by omitting the additional light source 74 for emitting violet light and providing the additional light source 201 instead of the additional light source 74.

Figure 18:
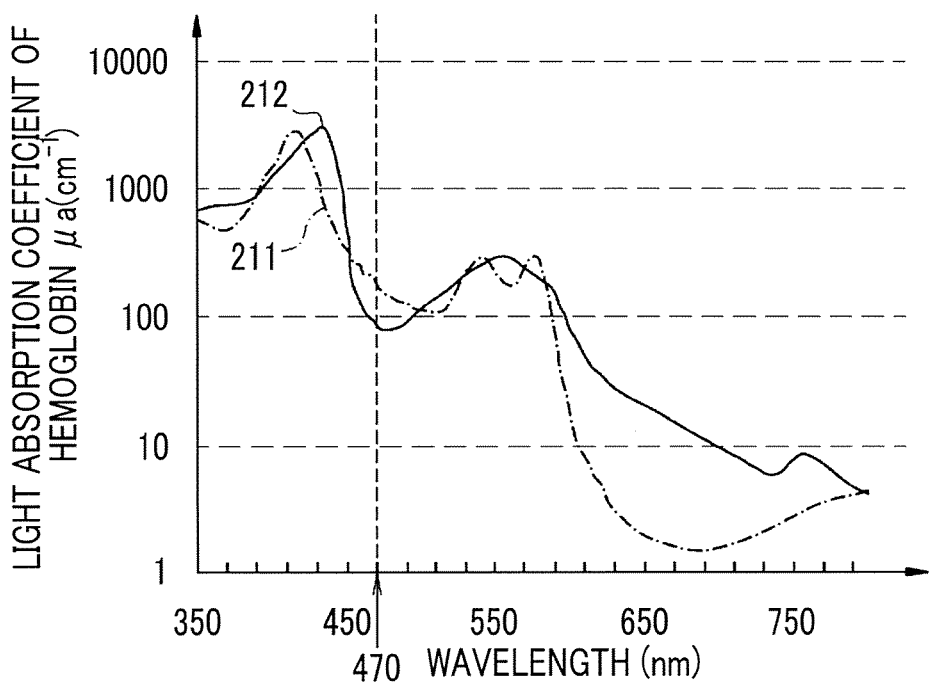
FIG. 18 is a graph showing the light absorption coefficients of oxygenated hemoglobin and reduced hemoglobin.

The additional light source 201 emits light having a difference in light absorption coefficient between oxygenated hemoglobin and reduced hemoglobin, for example. As shown in FIG. 18, light having a difference in light absorption coefficient between oxygenated hemoglobin (graph 211) and reduced hemoglobin (graph 212) is, for example, blue light having a wavelength of about 470±5 nm. By using the B image obtained by using the light having a difference in light absorption coefficient between oxygenated hemoglobin and reduced hemoglobin as the illumination light, it is possible to measure the oxygen saturation of the observation object. Therefore, if the additional light source 201 that emits light having a difference in light absorption coefficient between oxygenated hemoglobin and reduced hemoglobin is provided in addition to the first and second light sources 71 and 72, an oxygen saturation observation mode for measuring the oxygen saturation of the observation target can be added to the endoscope system 10.

The additional light source 201 may be a light source that emits infrared light. In this case, an infrared observation mode in which the observation target is observed with infrared light, fluorescence generated by the infrared light, or the like can be added to the endoscope system 10.

Figure 19:
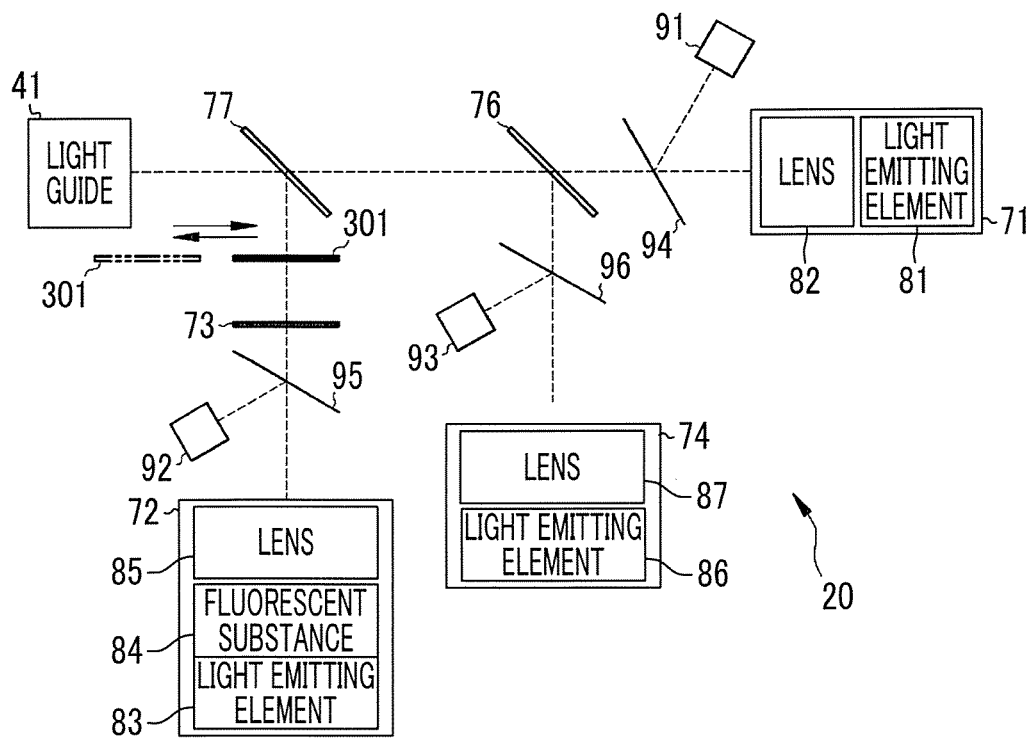
FIG. 19 is a block diagram of a light source unit in which not only an optical filter but also a second optical filter is provided.
Figure 20:
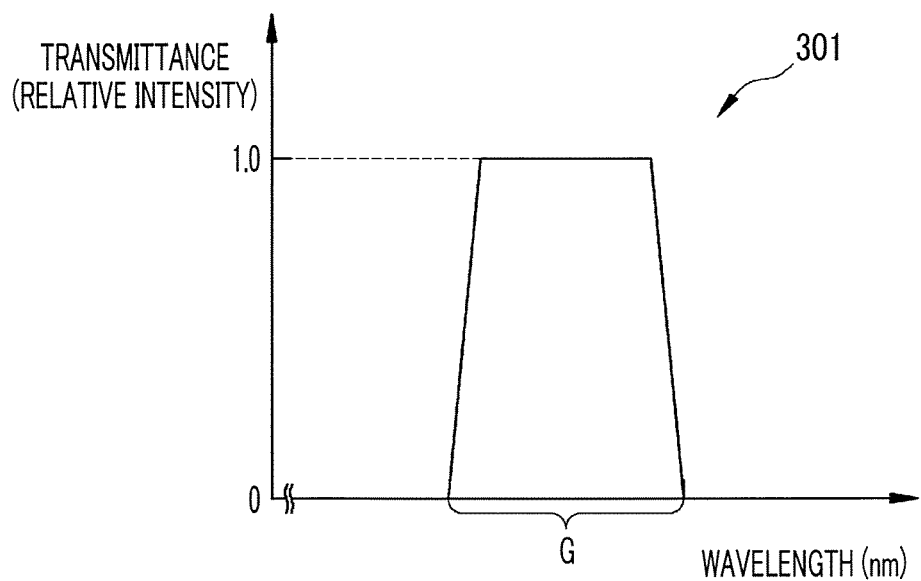
FIG. 20 is a graph showing the characteristics of the second optical filter.

As shown in FIGS. 19 and 20, it is preferable that the light source unit 20 includes a second optical filter 301 for attenuating the red component R of the broadband green light so as to be freely inserted into and removed from the optical path of the broadband green light in addition to the optical filter 73. If the second optical filter 301 for attenuating the red component R of the broadband green light is provided so as to be freely inserted and removed, an observation mode in which an R image is not required and an accurate B or G image having no mixed color of red light is required can be added to the endoscope system 10. The observation mode in which an R image is not required and an accurate B or G image having no mixed color of red light is required is, for example, an observation mode in which blood vessels at a specific depth or thickness are extracted and highlighted for observation based on the difference between the B image and the G image, the difference between the B image captured with the blue component B and the B image captured with the violet component V, and the like.

Figure 21:
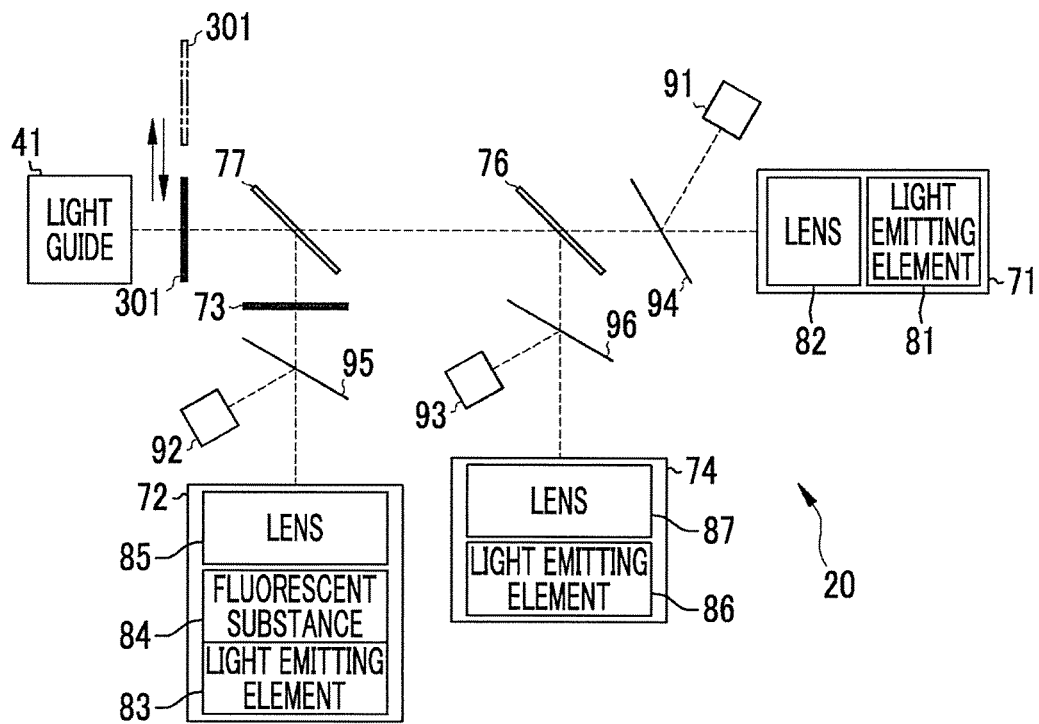
FIG. 21 is a block diagram of another light source unit in which not only an optical filter but also a second optical filter is provided.
Figure 22:
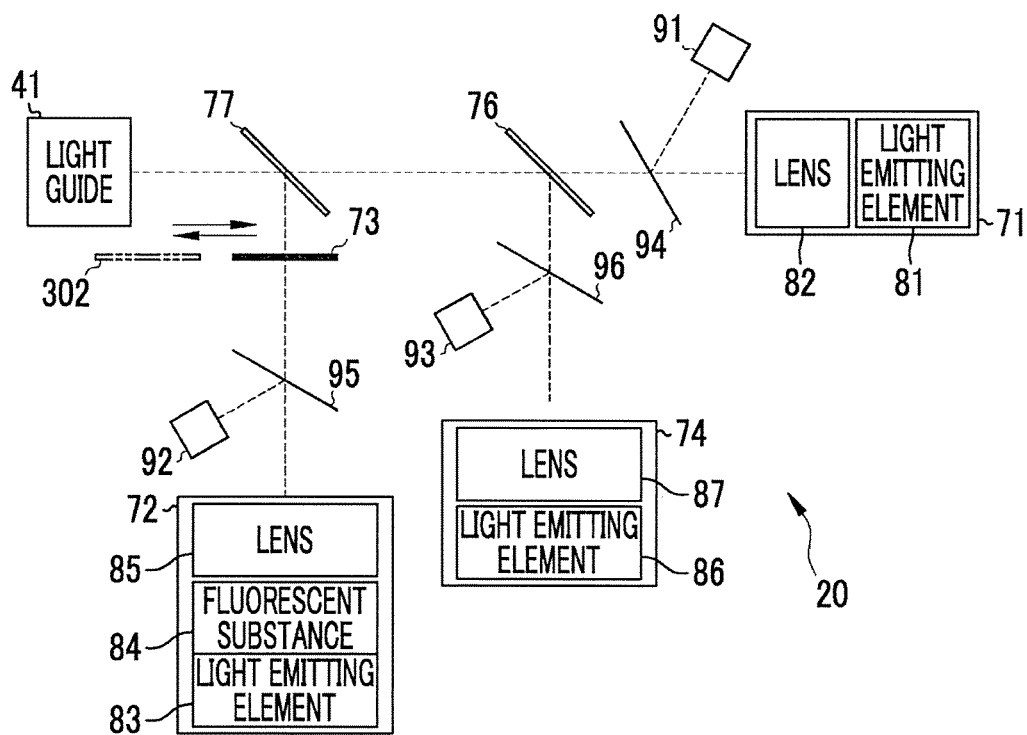
FIG. 22 is a block diagram of a light source unit in which a second optical filter is provided so as to be exchangeable with an optical filter.
Figure 23:
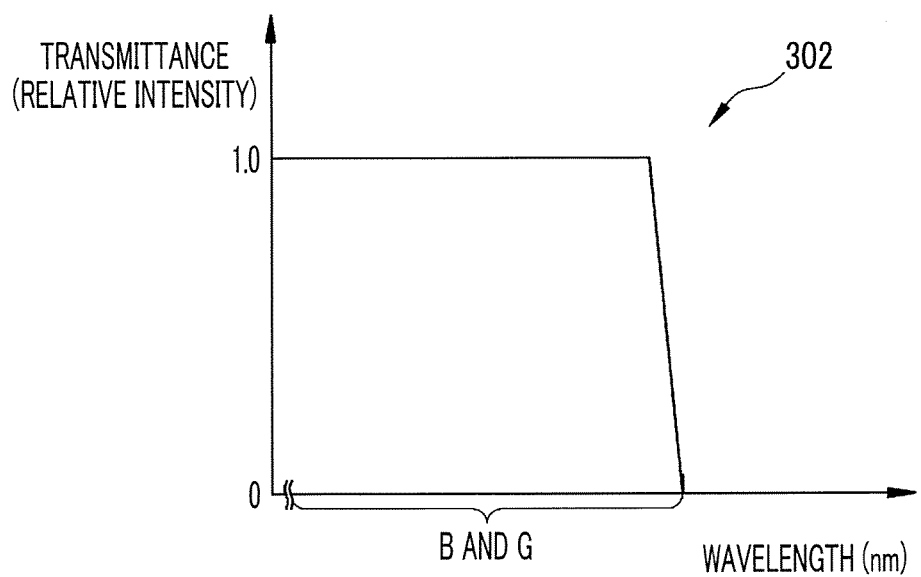
FIG. 23 is a graph showing the characteristics of the second optical filter provided so as to be exchangeable with an optical filter.

In FIG. 19, the second optical filter 301 is provided between the second light source 72 and the multiplexing member 77. However, as shown in FIG. 21, the second optical filter 301 may be provided on the downstream side (between the multiplexing member 77 and the light guide 41) of the multiplexing member 77. In FIG. 19, not only the optical filter 73 but also the second optical filter 301 is provided. However, instead of the second optical filter 301, a second optical filter 302 for attenuating the red component R from the broadband green light can be provided so as to be exchangeable with the optical filter 73 as shown in FIGS. 22 and 23. The insertion and removal of the second optical filters 301 and 302 are controlled by the light source control unit 22.

Figure 24:
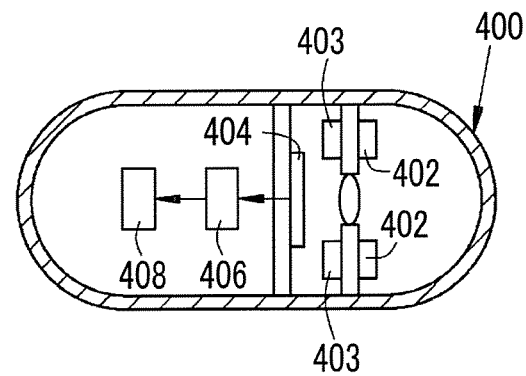
FIG. 24 is a schematic diagram of a capsule endoscope.

In the embodiment described above, the invention is implemented in the endoscope system in which the endoscope 12 including the image sensor 48 is inserted into the subject to observe the inside of the subject. However, the invention is also suitable for a capsule endoscope system. As shown in FIG. 24, for example, the capsule endoscope system includes at least a capsule endoscope 400 and a processor device (not shown).

The capsule endoscope 400 includes a light source unit 402, a control unit 403, an image sensor 404, an image processing unit 406, and a transmitting and receiving antenna 408. The light source unit 402 corresponds to the light source unit 20. The control unit 403 functions similarly to the light source control unit 22 and the control unit 69. The control unit 403 can perform radio communication with the processor device of the capsule endoscope system using the transmitting and receiving antenna 408. Although the processor device of the capsule endoscope system is almost the same as the processor device 16 in the embodiment described above, the image processing unit 406 corresponding to the image acquisition unit 54 and the image processing unit 61 is provided in the capsule endoscope 400, and the generated observation image is transmitted to the processor device through the transmitting and receiving antenna 408. The image sensor 404 is the same as the image sensor 48.

In the above-described embodiment and modification examples, the first light source 71, the second light source 72, the additional light source 74, and the additional light source 201 are all semiconductor light sources, such as LEDs. However, instead of these semiconductor light sources or in combination with any one of these semiconductor light sources, illumination lamps such as xenon lamps or other halogen lamps can be used in the light source device 14. A case is also included in which the optical filter is moved to the optical path and a specific wavelength region is selectively output from the light emitted from the illumination lamp.

Figure 25:
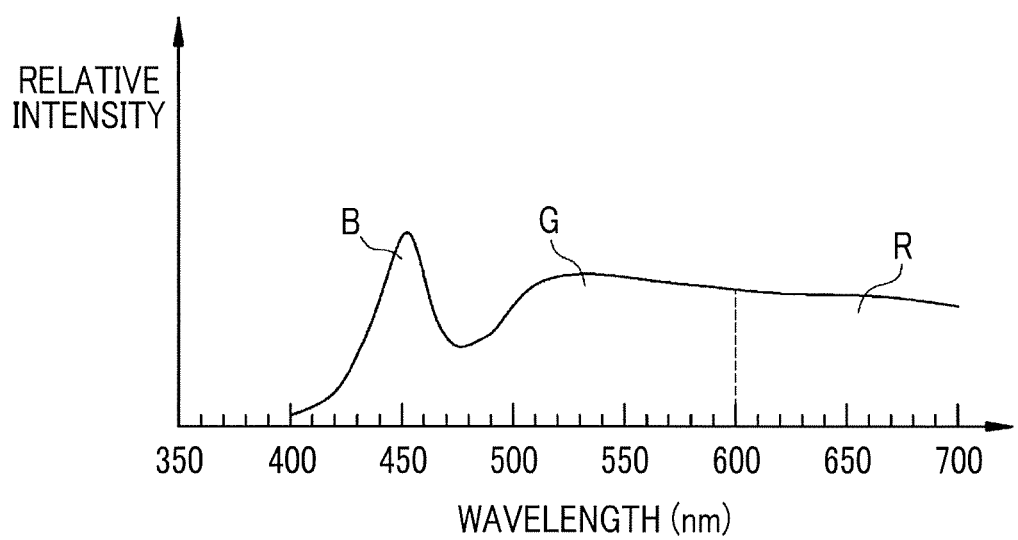
FIG. 25 is a spectral spectrum of white light emitted from a white LED.
Figure 26:
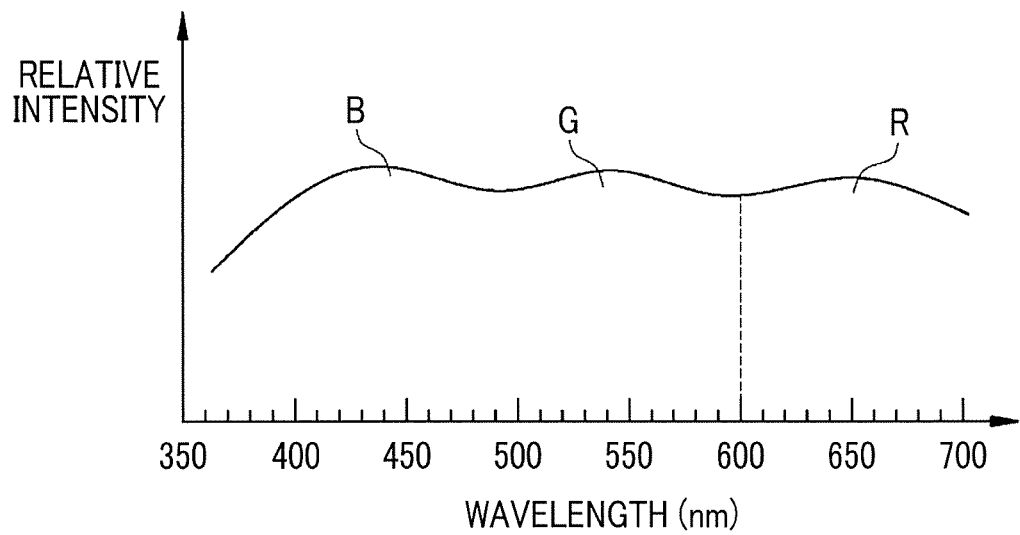
FIG. 26 is a spectral spectrum of white light emitted from another white LED.

In the above-described embodiment and modification examples, the second light source 72 emits broadband green light including the green component G and the red component R. However, the light emitted from the second light source 72 preferably includes at least the green component G and the red component R, and may further include the blue component B, the violet component V, an ultraviolet component, or an infrared component. For example, an LED that emits white light (so-called white LED) can be used as the second light source 72. The white light emitted from the white LED has, for example, a spectral spectrum shown in FIG. 25, and attenuation of the red component R is small in comparison with the broadband green light (refer to FIG. 5) of the embodiment and modification examples described above. For example, as shown in FIG. 26, there is a white LED that emits white light (white light with a good color rendering property) having a spectral spectrum close to natural light. The white LED that emits white light with a good color rendering property is suitable for the second light source 72.

In the above-described embodiment and modification examples, the first light source 71, the additional light source 74, and the additional light source 201 are configured to include the light emitting element 81 or 86 and the lens 82 or 87. However, similarly to the second light source 72, the first light source 71, the additional light source 74, and the additional light source 201 can also be configured to include a light emitting element that emits excitation light, a fluorescent substance that emits light to be emitted from each of the light sources described above when the excitation light is incident, and a lens for arranging the light emitted from the fluorescent substance into parallel light or the like. Conversely, the second light source 72 can be formed by a light emitting element and a lens similarly to the first light source 71 or the like if the second light source 72 can emit broadband green light. In addition, the first light source 71, the second light source 72, the optical filter 73, the additional light source 74, the multiplexing member 76, the photodetectors 91, 92, and 93, the beam splitters 94, 95, and 96, and each unit of the light source unit 20 such as the additional light source 201 can move along the optical axis.

In the above-described embodiment and modification examples, the optical filter 73 also functions as a multiplexing member of blue light or the like and broadband green light. However, the optical filter 73 can be provided separately from the multiplexing member of blue light or the like and broadband green light. In this case, the optical filter 73 may be disposed on the optical path from the broadband green light emitted from the second light source 72 to the light guide 41, and it is preferable that the optical filter 73 is disposed at a position before multiplexing with the blue light or the like.

EXPLANATION OF REFERENCES 10, 101: endoscope system
12: endoscope
12a: insertion portion
12b: operation portion
12c: bending portion
12d: distal end portion
12e: angle knob
13a: zoom operation portion
13b: mode selector switch
14: light source device
16: processor device
18: monitor
19: console
20, 402: light source unit
22: light source control unit
30a: illumination optical system
30b: imaging optical system
41: light guide
45: illumination lens
46: objective lens
47: zoom lens
48, 404: image sensor
54: image acquisition unit
56: DSP
58: noise reduction section
59: conversion section
61, 406: image processing unit
66: display control unit
69, 403: control unit
71: first light source
72: second light source
73: optical filter
74, 201: additional light source
76, 77: multiplexing member
81: light emitting element
82, 85, 87: lens
83: light emitting element
84: fluorescent substance
86: light emitting element
91, 92, 93: photodetector
94, 95, 96: beam splitter
98: illumination light
102: integrated control device
104: light source block
106: processor block
211: graph showing light absorption coefficient of oxygenated hemoglobin
212: graph showing light absorption coefficient of reduced hemoglobin
301, 302: second optical filter
400: capsule endoscope
408: transmitting and receiving antenna
B: blue
C: cyan
M: magenta
Ex: excitation light
G: green
R: red
V: violet
Y: yellow

What is claimed is:

1. A light source device, adapted to an endoscope system, comprising:
a first light source that emits blue light;
a second light source that emits broadband green light including not only a green component but also a red component; and
an optical filter that adjusts an amount of the broadband green light for each wavelength,
wherein the optical filter has a characteristic in which a reflectance of the green component is smaller than a reflectance of the red component in a case of reflecting the broadband green light or a characteristic in which a transmittance of the green component is smaller than a transmittance of the red component in a case of transmitting the broadband green light, wherein an overall reflectance of the broadband green light by the optical filter in the case of reflecting the broadband green light, or an overall transmittance of the broadband green light by the optical filter in the case of transmitting the broadband green light, gradually rises as the broadband green light increases in wavelength from a range of 600 nm to 680 nm in wavelength, wherein the transmittance of the green component for each wavelength in the optical filter is substantially constant, and the transmittance of the red component for each wavelength in the optical filter gradually rises smoothly after 550 nm towards the long wavelength side.

2. The light source device according to claim 1,
wherein the second light source includes a light emitting element that emits excitation light and a fluorescent substance that emits the broadband green light when the excitation light is emitted thereto, and
the optical filter cuts the excitation light.

3. The light source device according to claim 1,
wherein the optical filter has a reflectance or a transmittance for each component that changes stepwise.

4. The light source device according to claim 2,
wherein the optical filter has a reflectance or a transmittance for each component that changes stepwise.

5. The light source device according to claim 1,
wherein the optical filter has a reflectance or a transmittance for each component that changes smoothly.

6. The light source device according to claim 2,
wherein the optical filter has a reflectance or a transmittance for each component that changes smoothly.

7. The light source device according to claim 1,
wherein the optical filter is a multiplexing member that combines the blue light and the broadband green light.

8. The light source device according to claim 2,
wherein the optical filter is a multiplexing member that combines the blue light and the broadband green light.

9. The light source device according to claim 3,
wherein the optical filter is a multiplexing member that combines the blue light and the broadband green light.

10. The light source device according to claim 4,
wherein the optical filter is a multiplexing member that combines the blue light and the broadband green light.

11. The light source device according to claim 5,
wherein the optical filter is a multiplexing member that combines the blue light and the broadband green light.

12. The light source device according to claim 6,
wherein the optical filter is a multiplexing member that combines the blue light and the broadband green light.

13. The light source device according to claim 1, comprising, in addition to the first and second light sources:
an additional light source that emits light having a difference in light absorption coefficient between oxygenated hemoglobin and reduced hemoglobin.

14. The light source device according to claim 2, comprising, in addition to the first and second light sources:
an additional light source that emits light having a difference in light absorption coefficient between oxygenated hemoglobin and reduced hemoglobin.

15. The light source device according to claim 3, comprising, in addition to the first and second light sources:
an additional light source that emits light having a difference in light absorption coefficient between oxygenated hemoglobin and reduced hemoglobin.

16. The light source device according to claim 1, comprising, in addition to the first and second light sources:
an additional light source that emits infrared light.

17. The light source device according to claim 1, comprising, in addition to the optical filter or in an exchangeable manner with the optical filter:
a second optical filter that attenuates the red component from the broadband green light.

18. An endoscope system, comprising:
a light source device according to claim 1 which has a first light source that emits blue light, a second light source that emits broadband green light including not only a green component but also a red component, and an optical filter that adjusts an amount of the broadband green light for each wavelength and in which the optical filter has a characteristic, in which a reflectance of the green component is smaller than a reflectance of the red component in a case of reflecting the broadband green light, or a characteristic, in which a transmittance of the green component is smaller than a transmittance of the red component in a case of transmitting the broadband green light, wherein an overall reflectance of the broadband green light by the optical filter in the case of reflecting the broadband green light, or an overall transmittance of the broadband green light by the optical filter in the case of transmitting the broadband green light, gradually rises as the broadband green light increases in wavelength from a range of 600 nm to 680 nm in wavelength, wherein the transmittance of the green component for each wavelength in the optical filter is substantially constant, and the transmittance of the red component for each wavelength in the optical filter gradually rises smoothly after 550 nm towards the long wavelength side; and
an image sensor that images an observation target using the blue light and the broadband green light whose components have been adjusted by the optical filter.

19. The endoscope system according to claim 18,
wherein the image sensor is a color sensor having a color filter for each pixel.

20. The endoscope system according to claim 18,
wherein a gain applied to a red image obtained by imaging the observation target using the red component is larger than a gain applied to a green image obtained by imaging the observation target using the green component.

* * * * *